United States Patent [19]

Deghenghi et al.

[11] Patent Number: 4,824,937

[45] Date of Patent: Apr. 25, 1989

[54] SYNTHETIC NATRIURETIC PEPTIDES

[75] Inventors: Romano Deghenghi, Denens; Hans U. Immer, Balsthal, both of Switzerland

[73] Assignee: 501 Advanced Peptide Development, Ltd., Chingford, England

[21] Appl. No.: 50,208

[22] Filed: May 14, 1987

[30] Foreign Application Priority Data

May 20, 1986 [CA] Canada ................................. 509564

[51] Int. Cl.$^4$ .............................................. C07K 7/10
[52] U.S. Cl. ..................................................... 530/326
[58] Field of Search ........................................ 530/326

[56] References Cited

U.S. PATENT DOCUMENTS

| | | | |
|---|---|---|---|
| 4,496,544 | 4/1985 | Needleman | 530/326 |
| 4,557,864 | 12/1985 | Needleman | 530/326 |
| 4,607,023 | 8/1986 | Thibault et al. | 530/326 |
| 4,670,540 | 6/1987 | Sakakibara | 530/326 |
| 4,716,147 | 12/1987 | Tjoeng et al. | 530/326 |

FOREIGN PATENT DOCUMENTS 3614833 7/1987 Fed. Rep. of Germany.

*Primary Examiner*—Delbert R. Phillps
*Assistant Examiner*—Christina Chan
*Attorney, Agent, or Firm*—Omri M. Behr

[57] ABSTRACT

Synthetic natriuretic peptides (SNP) composed of 23 amino acid residues of which residues 2–23 have the natural L-configuration while the amino-terminal residue is derived from an unnatural amino acid having the D-configuration. The compounds possess diuretic, natriuretic, vasorelaxant, smooth muscle relaxant, hypotensive, and anti-hypertensive activities, and a process for their preparation is also disclosed, together with pharmaceutical preparations thereof and with their use in the practice of medicine. Salts of said synthetic natriuretic peptides with pharmaceutically acceptable acids are also disclosed.

7 Claims, No Drawings

SYNTHETIC NATRIURETIC PEPTIDES

BACKGROUND OF THE INVENTION (a) Field of the Invention

The present invention relates to synthetic natriuretic peptides possessing diuretic and natriuretic activities of a very high color order as well as vasorelaxant and smooth muscle relaxant properties together with hypotensive activities in normotensive mammals and anti-hypertensive activities in renovascular hypertensive mammals. Those synthetic natriuretic peptides contain 23 amino acid residues, with residues 2–23 having the natural or L-configuration while the amino-terminal residue is derived from an unnatural amino acid having the D-configuration. This invention also relates to a process for preparing the above compounds having either a free carboxylic acid or a carboxylic acid amide group at the carboxy-terminal, as well as to pharmaceutical preparations containing the above synthetic natriuretic peptides in their free state or as salts with pharmaceutically acceptable acids, and to the use of said pharmaceutical preparations as diuretic and/or natriuretic agents, as vasorelaxants and/or smooth muscle relaxants, and as anti-hypertensive agents in mammals suffering from renovascular hypertension.

(b) Description of Prior Art

Numerous papers have been published since A. J. de Bold et al., 1981 Life Sci. 28, 89 reported that extracts of rat myocardial tissue caused a strong and rapid rise in uninary output and an equally dramatic rise in the excretion of sodium and of chloride when administered intraveneously to non-diuretic rats, with a concomitant decrease in blood pressure; the authors concluded that the extracts contained and extremely powerful inhibitor of renal tubular NaCl reabsorption. Evidence for the polypeptide nature of said inhibitor and the results of preliminary purification showing multimodal distribution were presented by de Bold, 1981 Fed. Proc. 40, 554 and 1982 Proc. Soc. Exp. Biol. Med. 170, 133. Trippodo et al., ibid. p. 502 and 1983 Hypertension 5, Suppl. I, I-81 reported that the above inhibitor or atrial natriuretic factor (ANF) was present in rat, rabbit, dog, baboon, and human atrial extracts and found activity mainly in two fractionation ranges, viz., 36000–44000 and 3600–5500 daltons. Currie et al., 1983 Science 221, 71 showed that rat, pig, and human atrial extracts possessed natriuretic and powerful vasorelaxant and smooth muscle relaxant activities. Further studies on the purification and the composition of rat ANF by de Bold et al., 1983 Life Sci. 33, 292, by Grammar et al., 1983 Biochem. Biophys. Res. Comm. 116, 696, and by Thibault et al., 1983 FEBS Letters 164, 286 resulted in the isolation of peptides composed of 49, 36, and 26, 31, and 33 amino acids, respectively. Flynn et al., 1983 Biochem. Biophys. Res. Comm. 117, 859 succeeded in establishing the sequence of a rat ANF composed of 28 amino acid residues; Currie et al., 1984 Science 223, 67, and Geller et al., 1984 Biochem. Biophys. Res. Comm. 120, 333 isolated and determined the sequences of a number of rat atrial peptides ("atriopeptins") containing 19–24 amino acid, see also U.S. Pat. No. 4,964,544 issued Jan. 29, 1985. Misono et al., 1984 Biochem. Biophys. Res. Comm. 119, 524 isolated a rat ANF containing 25 amino acids and determined its sequence; they found that the presence of the disulfide linkage between the two half-cystine residues was essential for natriuretic, diuretic, and vasorelaxant activitives. Seidah et al., 1984 Proc. Natl. Acad. Sci. USA 81, 2640 prepared and sequenced four ANF obtained from rat tissue and determined their sequences; they were found to contain 33, 32, 31, and 26 amino acid residues, respectively; the authors also succeeded in synthesizing said last-named ANF by coupling four fragments thereof by means of classical method, with each of the above fragments having been prepared by solid-phase synthesis. Garcia et al., 1984 Biochem. Biophys . Res. Comm. 119, 685 reported that the native ANF with 26 , amino acids and the above synthetic ANF, both as the C-terminal carboxylic acid and as the corresponding acid amide, had identical vasorelaxant activities; furthermore, Napier et al., 1984 Biochem. Boiphys. Res. Comm. 120, 981 confirmed the results of Seidah et al. cited above with respect to the native ANF having 33, 32, and 31 amino acid residues, respectively, and established that those compounds had free carboxylic acid groups at the C-terminus. Atlas et al., 1984 Nature 309, 717 isolated and sequenced a rat ANF having 24 amino acid residues ("auriculin A") which was also prepared by solid-phase synthesis. A C-terminal extended form thereof having an additional tyrosine residue ("auriculin B") was also detected. Sugiyama et al., 1984 Biochem. Biophys. Res. Comm. 123, 338 prepared by solid-phase synthesis the rat ANF containing 25 amino acids first described by Misono et al. cited above, as well as atriopeptin I having 21 amino acids first described by Currie et al. cited above. Thibault et al., 1984 Biochem. Biophys. Res. Comm. 125, 938 subjected to synthetic ANF having 26 amino acid residues described by Seidah et al. cited above to Edman degradation and obtained the corresponding N-terminal truncated ANF having 25, 24, 23, and 22 amino acids, respectively; digestion of the above synthetic ANF with various carboxypeptidases gave the corresponding C-terminal truncated ANF containing 25, 24, 23, and 21 amino acids, respectively. Kangawa et al., 1984 Biochem. Biophys. Res. Comm. 118, 131 used human atrial tissue as the starting mayterial and succeeded in isolating, sequencing, and synthesizing by a solid-phase procedure a peptide (α-hANP) containing 28 amino acid residues; α-hANP was found to have the same sequence as the 28-amino acid peptide obtained from rat atria by Flynn et al. cited above, except that is contained a methionine residue in position 7 (position 110, see below) where the peptide of Flynn et al. and all other ANF obtained from rat atria disclosed in the above references have an isoleucine residue.

Concerning the numbering of individual residues in the various atrial natriuretic peptides (ANP) described in the above references it was customary to number them consecutively starting with the N-terminal residue as No. 1. However, following the successful cloning of rat and of human cDNA and of the respective genes for ANP, it is now the international consensus to number the respective propeptides consecutively from $Asn^1$ to $Tyr^{126}$ so as to establish an unambiguous numbering system.

The synthetic natriuretic peptides (SNP) of this invention are characterized by containing only 23 amino acid residues, of which residues 2–23 have the natural or L-configuration while the amino-terminal residue is that of an unnatural D-amino acid. We have found, surprisingly, that the synthetic natriuretic peptides of this invention possess the full range of biological activities found in known natriuretic peptides having larger numbers of amino acid residues in their respective molecules, and that they are particularly distinguished by possessing natriuretic and aortic vasorelaxant properties of a high order. However, a totally unexpected property of the SNP of this invention is their significant dissociation between diuretic and natriuretic activity on the one hand which is fully present therein, and their vasorelaxant activity on the other hand which is found to be present to a smaller degree. This surprising dissociation of activities exhibited by the above SNP provides important therapeutic advantages, in that the undesirable effects upon heart rate which are a common feature of known atrial natriuretic factors (ANF) or atrial natriuetic peptides (ANP), viz., either bradycardia or tachycardia, are significantly diminished. The fact that the SNP of this invention are composed of only 23 amino acid residues results in the further advantage that their preparation by classical methods, or preferably by solid phase synthesis, in simpler, more easily performed, and more economical than that of known natriuretic peptides. The particular process of this invention offers the additional advantage that the products are obtained in good yields with a high degree of purity, and that they may be produced at will either in the form of their respective free carboxylic acid or as the corresponding carboxylic acid amide. Both types of the synthetic natriuretic peptides of this invention are useful as research tools, and are particularly useful in the practice of medicine for the treatment of patients suffering from pathological conditions associated with abnormalities in their water and electrolyte balances, for example as diuretic and natriuretic agents, as vasorelaxant and/or smooth muscle relaxant agents, or as hypotensive or anti-hypertensive agents, the latter especially in patients suffering from hypertension of renovascular origin, as well as in cases of congestive heart failure and of edema. Moreover, the synthetic natriuretic peptides of this invention offer the added and surprising advantage of showing a longer duration of action than known natriuretic peptides. The fact that many of the native ANF have been obtained as amino-terminal truncated versions of longer peptides seems to indicate that the mammalian organism contains certain proteases which attack the latter peptides from the amino terminus. The longer duration of action shown by the synthetic natriuretic peptides of this invention is attributed to the protection offered against such proteolytic attack by the presence of an unnatural D-amino acid at their respective amino terminus.

In the following text the symbols for the amino acids are according to the IUPAC-IUB recommendations, see Arch. Biochem. Biophys. 115, 1 (1966). The symbols for the protective groups used in he synthesis process are those described in Shroöder and Lübke, "The Peptides", Academic Press, New York and London, 1965, as well as in the current literature. Other abbreviations used are e.g., SNP: synthetic natriuretic peptide(s); ANP: atrial natriuretic peptide(s); ANF: atrial natriuretic factor(s); TFA: trifluoroacetic acid; DMF: dimethylformamide; TEA: triethylamine; DIEA: diisopropylethylamine; HPLC: high pressure liquid chromatography; RP-HPLC: reverse phase high pressure liquid chromatography. Other symbols and/or abbreviations are those commonly used in peptide chemistry and will readily be understood by those skilled in the art. The following terms are Registered Trade Marks or Trade Names: Sephadex; Vydac.

SUMMARY OF THE INVENTION

The synthetic natriuretic peptides (SNP) of this invention are represented by the following formula (1)

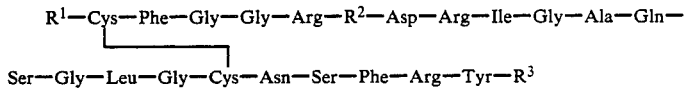

in which $R^1$ represents the residue of the D-form of an amino acid which is commonly found in nature with the L-configuration, namely: Ala, Arg, Asn, Asp, Cys, Gln, Glu, His, Ile, Leu, Lys, Met, Phe, Pro, Thr, Trp, Tyr, Val, or the residue of D-form of amino acid which is not commonly found in nature with the L-configuration, for example D-phenylglycine (D-PheGly) or D-tert-butylglycine (D-tBu Gly) (D-2-amino-3,3-dimethylbutyric acid), $R^2$ is selected from Ile and Met, and $R^3$ represents OH or $NH_2$.

The compounds of this invention are prepared by solid phase synthetic methods as described, e.g., in J. M. Stewart and J. O. Young, "Solid Phase Peptide Synthesis", 2. Ed., Pierce Chemical Company, 1984, using a 4-(hydroxy methyl)-phenylacetamidomethyl (PAM) resin to prepare the peptides of formula 1 in which $R^3$ is OH and a 4-methylbenzhydrylamine resin to prepare the peptides of formula 1 in which $R^3$ is $NH_2$.

The alpha-amino group of the amino acids used in the synthetic procedure is protected by the t-butyloxycarbonyl (Boc) group, the beta-carboxylic acid group of aspartic acid is protected as the benzyl ester, the hydroxy group of serine is protected as the benzyl ether, the phenolic hydroxy group of tyrosine and the epsilon amino group of lysine are protected by the 2-bromobenzyloxycarbonyl group, the guanidino group of arginine is protected by the tosyl group, and the sulfhydryl group of cysteine is protected by the 4-methylbenzyl group. protected amino acids are coupled using a two-fold excess of their respective preformed symmetrical anhydrides except for Boc-Asn, Boc-Gln, and Boc-Arg(Tos) which are coupled as their respective preformed hydroxybenzotriazole (HOBT) esters. Following each coupling step, cleavage of the Boc protective group is effected with 50% trifluoroacetic acid in methylene chloride, followed by neutralization with N,N'-diisopropylethylamine in methylene chloride. Cleavage of the completed peptide from the resin support together with cleavage of the protective groups listed above is effected by treatment with HF/anisole (9:1) with cooling in an ice bath, followed by precipitation in ether, filtration, dissolving the solid in 80% acetic acid, filtration, dilution with water, and freeze-drying. The residue thus obtained is dissolved in water, the pH is adjusted to 6–7, and a molar excess of potassium ferricyanide is added. The resulting mixture is agitated, treated with an anion exchange resin in the acetate form, filtered, and freeze-dried. The resulting solid is dissolved in 50% acetic acid, desalted on a column of Sephadex G-15, and the eluates are freeze-dried to obtain the crude peptide as the acetate salt. Final purification is done by preparative RP-HPLC on silica bonds coated with a diphenyl octadecylsilane (Vydac C-18, 15–20 micron, 200 A, reverse phase) using a solvent system consisting of (A): 0.25N $H_3PO_4$ titrated to pH 2.25 with triethylamine, and (B): solvent (A) and $CH_3CN$ 40:60, by gradient elution. Optimal slope and end points of the gradient are determined from an analytical run, and the individual fractions obtained from the preparative column are monitored on an analytical column, by RP-HPLC as above, to ascertain their purity. Fractions containing the pure peptide are desalted on a column of Sephadex G-15 by RP-HPLC with acetic acid/acetonitrile and freeze-dried, to obtain the pure synthetic natriuretic peptide of this invention in the form of its acetate salt. The purity of said last-named peptide is further ascertained by analytical RP-HPLC and by amino acid analysis.

DETAILED DESCRIPTION OF THE INVENTION

I. Biological Assays

The diuretic activities of the synthetic natriuretic peptides (SNP) of this invention and their effects upon electrolyte excretion are determined in male normotensive Sprague-Dawley rats. The animals are anesthetized with sodium pentobarbital (55 mg/kg), the femoral vein is cannulated for injection of the test compound and for infusion of Ringer's solution, the bladder is cannulated for urine collection, and the trachea is cannulated to ensure a clean airway. The animals are infused with Ringer's solution at a rate of 1.2 ml/20 min. for 20 minutes, the infusion rate is then decreased to 1.2 ml/hour for a further 20 minutes, and urine collections are started at the end of that period. Three 10-minute collections are taken as control samples, and at the end of the third 10-minute period the SNP to be tested is injected as a bolus over 30 seconds into the femoral vein. Infusion of Ringer's solution at 1.2 ml/hour is continued for the duration of the experiment, and urine samples are collected every 10 minutes over 4 hours, their respective volumes are determined, and the concentrations of $Na^+$, $Cl^-$, and $K^+$ are measured using a NovaBiomedical electrolyte analyzer. The above determinations are done on samples pooled from all animals in a given experiment, and urine flow is calculated as ml/min./kg body weight while electrolyte concentrations are calculated as mmol/l/gm kidney tissue. The SNP of this invention are highly active in the above tests, with doses in the nanomole range causing pronounced diuresis and increases in $Na^+$ and $Cl^-$ excretion comparable to the highly potent ANP used as reference compound.

The vasorelaxant activities of the SNP of this invention are determined in vitro using freshly prepared rabbit thoracic aorta strips, helically cut according to the method of Furchgott et al., 1953 J. Pharmacol. Exp. Therap. 108, 129. One end of each strip is attached to a holding rod, the other end is equipped with a silk thread which is kept under a tension of about 5 g, and the complete assembly is kept over night at 4° C. in oxygenated Krebs solution. On the day of the experiment each strip is set up in a 10 ml bath of oxygenated (5% $CO_2$) Krebs solution at 37° C. and the thread is attached to an isometric force transducer (Grass Instruments Model FT.03) connected to a polygraph (Grass Instruments Model 5). A resting tension of 5 g is applied to each strip and is readjusted until a stable resting tension is attained (45–60 minutes). The strips are then challenged repeatedly with the same dose of noradrenaline to ensure that the induced increase in tension is uniform. The stock solution of noradrenaline bitartrate (Sigma Chemical Co.) is made up in 0.001N HCl, and dilutions are freshly prepared in deionized water containing 0.0001M ascorbic acid and are kept protected from light during the experiments. In each experiment two cumulative full dose-response determinations to noradrenaline alone are carried out consecutively on one strip (time control). On the other strips dose-response determinations are done with noradrenaline alone, and then repeated five minutes after having added the compound to be tested to concentrations of 2, 5, 50, and 500 ng/ml, respectively. The tension elicited by each concentration of noradrenaline is expressed as a percentage of the maximal response obtained with noradrenaline, and the concentration of noradrenaline producing a tension equal to 50% of the maximal response is calculated (EC50). The same calculations are also carried out with the results obtained in the presence of the various concentrations of the compound to be tested, and the EC50 thus obtained is divided by the EC50 obtained in the absence of said compound, to arrive at a ration which is clear indication of the potency of the respective compound. The SNP of this invention are thus shown to be powerful vasorelaxant agents with a range of activities comparable to those of the reference compound, but significantly different therefrom by showing the unexpectedly favourable dissociation of activities discussed above.

II. Synthesis

As mentioned above, the SNP of this invention are prepared by solid-phase synthetic methds using a 4-(hydroxymethyl)phenylacetamidomethyl (PAM) resin to prepare the SNP of formula 1 in which $R^3$ is OH, and a 4-methylbenzhydrylamine resin to prepare the SNP of formula 1 in which $R^3$ is $NH_2$. The $\alpha$-amino group of all the amino acids used in the synthesis is protected by the t-butyloxycarbonyl (Boc) group, and the protective groups for the secondary functional groups which are present in some of the amino acids are selected in such a manner that they may all be removed by the same agent which is used for cleaving the SNP from the resin support; preferred protective groups are the benzyl ester for the $\beta$-carboxyl group of aspartic acid, the benzyl ether for the $\beta$-hydroxyl group of serine, the 2-bromobenzyloxycarbonyl group for the phenolic hydroxy group of tyrosine, the tosyl group for the guanidino group of arginine, and the 4-methylbenzyl group for the sulfhydryl group of cysteine. Following attachment of the protected C-terminal amino acid, viz., Boc-Tyr(2-bromobenzyloxycarbonyl) to the resin support, preferably by a procedure similar to that described by Yamashiro et al. in J. Am. Chem. Soc. 1973, 95, 1310, the protected amino acids are coupled using a two-fold excess of their respective preformed symmetrical anhydrides, which are in turn prepared by reacting the respective protected amino acid with dicyclohexylcarbodiimide (DCC). However, Boc-Asn, Boc-Gln, and Boc-Arg(Tos) are coupled as their respective preformed hydroxybenzotriazole (HOBT) esters, which are in turn prepared by reacting in solution in DMF the respective protected amino acid with hydroxybenzotriazole and DCC. Double couplings are routinely used whenever the HOBT esters of the protected amino acids are used. In all coupling steps the Boc protective group at the N-terminal of the amino acid or peptide attached to the resin support is cleaved with 50% TFA in methylene chloride followed by neutralization with N,N'-diisopropylethylamine (DIEA) before coupling the subsequent protected amino acid. Multiple washings with methylene dichloride are carried out following the above-mentioned cleavage of the Boc protective group with 50% TFA, prior to the subsequent coupling step. When all the amino acids required to form the desired peptide have been coupled as described above cleavage from the resin support with concomitant cleavage of the secondary protective groups is performed by suspending the peptide-resin in anisole, adding hydrogen fluoride to obtain a ratio of HF/anisole of 9:1, keeping the mixture in an ice bath for 30–60 minutes, preferably for 45 minutes, evaporating the HF, pouring the residue into a large volume of cold ether, and filtering the resulting solid mixture of peptide (SNP) and resin. Taking up the above solid mixture in aqueous acetic acid, filtering off the resin, diluting the filtrate with water and freeze-drying yields the crude SNP which is purified as described below.

It has been found to be particularly advantageous to perform the above synthesis on a Peptide Synthesizer Model 430A (Applied Biosystems, Foster City, CA) using the appropriate resin supports supplied by the same Company, viz., 4-(hydroxymethyl)-phenylacetamidomethyl (PAM) resin to prepare the SNP of formula 1 in which $R^3$ is OH and 4-methylbenzyhydrylamine resin to prepare the SNP of formula 1 in which $R^3$ is $NH_2$. The chemistry and the relative advantages of the above resin supports are described in Stewart and Young, "Solid Phase Peptide Synthesis", cited above.

The salient advantages of the above peptide synthesizer are first of all that different types of reactions and/or operations are carried out in separate vessels, so that the possibility of carrying over unwanted by-products or reactants into a subseequent step is virtually eliminated, resulting in cleaner operations and in products of higher purity. Second, transfers from one vessel to the other, as well as the reactions themselves, are carried out under nitrogen, so that the deleterious influence of atmospheric oxygen is eliminated. In principle, activation of the protected amino acid to be coupled is carried out in the activator vessel, followed by the appropriate wash cycles. The resulting solution of the activated protected amino acid is then transferred by nitrogen pressure to the concentrator vessel where the solvent is removed and replaced by the appropriate solvent in which the coupling is to be performed, and the resulting solution is transferred by nitrogen pressure to the reaction vessel. During the time taken for activation and concentration of the above protected amino acid to be coupled the N-terminal protective Boc group of the amino acid or peptide attached to the resin support in the reaction vessel is cleaved with 50% TFA and neutralized as described above, the solids are washed repeatedly with draining of the washings each time, so that the amino acid or peptide attached to the resin support is ready to receive the activated amino acid to be coupled in the reaction vessel where the coupling then takes place. More specifically, the symmetrical anhydrides of the protected amino acids used in the preparation of the SNP of this invention are prepared in the activator vessel in solution in methylene dichloride by reaction with DCC. Following the appropriate wash cycles the resulting solution of the symmetrical anhydride is transferred to the concentrator vessel where the methylene dichloride is removed and replaced by DMF, and the resulting solution is transferred to the reaction vessel where the coupling then takes place. On the other hand, when it is desired to use the 1-hydroxybenzotriazole esters of certain protected amino acids for coupling, the latter are prepared in the activator vessel in solution in DMF by reaction with HOBT and DCC followed by the appropriate washings with DMF. In those cases it is not necessary to use the concentrator, and the resulting solutions are directly transferred from the activator to the reaction vessel for coupling with the respective amino acid or peptide attached to the resin support. As said above, double couplings are systematically carried out with the above HOBT esters, and all the above reaction and wash cycles are performed according to the specific programs supplied by the Company for each individual amino acid. Moreover, the above peptide synthesizer is dimensioned so as to perform its operation with 0.5 mmole of the first amino acid in a given peptide synthesis, and all quantities of solvents are automatically delivered to suit those conditions and are also automatically adjusted to conform to the increase in volume of the peptide-resin due to the incorporation of amino acids in due succession. For example, when starting with 0.6–0.7 g of the resin support and preparing a peptide containing 20 amino acid residues there are obtained 2.5–3.0 g of the peptide-resin. Cleavage of the peptide from the resin support together with cleavage of the secondary protective groups is preferably carried out in a special HF apparatus (Peptide Institute Inc., Osaka 562, Japan), by suspending the peptide-resin in an equal volume of anisole, cooling the above suspension in a dry ice/methanol bath, distilling 9 volumes of dry HF into the reactor, and then keeping the mixture at about 0° C. in an ice bath for 30–60 minutes, preferably for about 45 minutes. At the end of that period the mixture is again cooled in a dry ice/methanol bath and is then dropped into 35–40 volumes of ether previously cooled to −20° C., and filtered. The solid precipitate, a mixture of the desired peptide and resin support, is suspended in about 20 volumes of 80% aqueous acetic acid, filtered to remove the resin support, the filtrates are diluted with water and freeze-dried to obtain a residue, viz., the desired peptide in its open-chain, non-cyclized form. In order to cyclize the last-named peptide by establishment of the disulfide bridge between its two cysteine residues so as to obtain the corresponding SNP the residue obtained above after freeze-drying is dissolved in water, adjusted to pH 6–7, and an aqueous solution of 0.05N potassium ferricyanide is carefully added until the yellow colour persists. The resulting solution is stirred with an anion exchange resin in its acetate form, preferably IRA 402 (Rohm & Haas, Philadelphia, PA) in its acetate form, filtered, and the filtrates are freeze-dried. The residue thus obtained is dissolved in 50% aqueous acetic acid, desalted by passing said solution over a column o Sephadex G-15 (Pharmacia A.B., Uppsala, Sweden), and the eluates containing the desired SNP are freeze-dried to obtain said SNP in a crude state.

Final purification of the crude SNP obtained as described above is achieved by RP-HPLC on a Waters Prep 500 apparatus (Waters Associates, Melford, MA) using a cartridge filled with silica beads coated with a diphenyl octadecylsilane (Vydac C-18, 15–20 microns, 300 A, obtained from The Separation Group, Hespado, CA) by gradient elution with the following solvent system:

Solvent "A": 0.25N $H_3PO_4$ titrated to pH 2.25 with triethylamine;

Solvent "B": solvent "A" and acetonitrile 40:60.

Optimal conditions for conducting the above RP-HPLC are established by taking frequent samples of the effluent from the above preparative apparatus and analyzing each sample separately by RP-HPLC on an analytical-size apparatus, preferably a Varian Model LC5500 apparatus (Varian Instruments, Palo Alto, CA) equipped with a Vydec C-18, 5 micron 300A column. Monitoring at 215 nm and determining the purity of the above samples establishes the optimal conditions of flow as well as the slope and the end points of the gradient, and in this manner the desired SNP is obtained as a pure compound after removal of the solvents. It is either taken up in 50% aqueous acetic acid and desalted on a column of Sephadex G-15 by elution with 20% acetonitrile in 50% aqueous acetic acid, or preferably it is taken up in 5% aqueous acetic acid and desalted on the same type of cartridge as used above with the Waters Prep 500 apparatus (Vydac C-18, 15–20 micron, 300A) by elution with 5% acetontirile in 5% aqueous acetic acid. In both cases the eluates are diluted with water and freeze-dried, to obtain the substantially pure SNP as its acetate salt. The purity of the above SNP is further ascertained by RP-HPLC on an analytical column as described above, and its composition is confirmed by amino acid analysis. The desired SNP is thus obtained in the form of its acetate salt with a purity of better than 99.8%.

The SNP of this invention are powerful diuretic, natriuretic, vasorelaxant, hypotensive, and anti-hypertensive agents and are useful in the treatment of pathological conditions associated with water and/or electrolyte imbalances as well as in hypertension, especially in renovascular hypertension. They are substantially non-toxic and have the added advantage of providing the desired effects at very low dosage levels. Although the compounds themselves are water-soluble at the very low concentrations at which they are usually employed they are preferably used in the form of their freely water-soluble acid addition salts with pharmaceutically acceptable acids, e.g. acetic, citric, malic, or succinic acid. The acetate salts are particularly advantageous because they are easily obtained as the products of the synthesis process described above. Such freely water-soluble salts may be converted if desired, into different acid addition salts with pharmaceutically acceptable acids, by treatment with the appropriate ion exchange resin in the manner described by Boissonas et al., 1960 Helv. Chim. Acta 43, 1349. Suitable ion exchange resins are strongly basic anion exchange resins, for example those listed in Greenstein and Winitz "Chemistry of the Amino Acids", John Wiley & Sons, Inc., New York and London 1961, Vol. 2, p. 1456. Basically substituted cross-linked polystyrene resins such as Amberlite IRA-400 or IRA-410 are preferred. Freely water-soluble salts of the SNP of this invention may also be converted to salts of low solubility in body fluids by treatment with a slightly water-soluble pharmaceutically acceptable acid, e.g. tannic or pamoic acid. In general, the acid addition salts of the SNP of this invention with pharmaceutically acceptable acids are biologically fully equivalent to the SNP themselves.

When the SNP of this invention or their acid addition salts with pharmaceutically acceptable acids are employed in medicine they are administered systemically, either by intravenous, subcutaneous, or intramuscular injection, or by sublingual or nasal administration, in compositions in conjunction with pharmaceutically acceptable vehicles or carriers. For administration by injection or by the nasal route it is preferred to use the SNP in solution in a sterile aqueous vehicle which may also contain other solutes such as buffers or preservatives as well as sufficient quantities of pharmaceutically acceptable salts or of glucose to make the solution isotonic. In addition, when the above compositions are intended for use as sprays for nasal administration they may also contain small amounts of pharmaceutically acceptable surface-active agents to ensure rapid absorption of the respective SNP by the nasal mucosa. For sublingual administration it is preferred to formulate the SNP of this invention as rapidly dissolving tablets together with solid excipients or carriers such as lactose. Examples of such excipients or carriers are found in standard pharmaceutical texts, e.g. in Remington's Pharmaceutical Sciences Mack Publishing Company, Easton, PA. 1970. Intranasal or sublingual administration may be less precise than intravenous injection but it may be a more convenient form of treatment.

When administration of the SNP of this invention is desired for the obtention of diuretic, natriuretic, vasorelaxant, hypotensive, or anti-hypertensive effects such as for example in the treatment of hypertension, in particular of renovascular hypertension, the dosage to be administered will depend upon such factors as the species, age, weight, sex, and condition of the patient, and with the chosen form of administration. Generally, treatment is initiated with small dosages substantially less than the optimal dose of the respective SNP. Thererafter, the dosage is increased by small increments until the optimal effect under the given circumstances is reached. In general, the SNP of this invention are most desirably administered at dosage levels which will give effective concentrations of the respective SNP in the blood of the patient without causing any harmful or deleterious side effects, and preferably at a level which is in the range from about 0.01 mcg to about 100 mcg per kilogram body weight, although as aforementioned variations will occur. However, a dosage level which is in the range of from about 0.1 mcg to about 25 mcg per kilogram body weight is most desirably employed to achieve effective results.

It is often desirable to administer the SNP of this invention continuously over prolonged periods of time, and one way by which this may be achieved is by administration of long-acting, slow-release, or depot dosage forms. Such dosage forms may either contain a pharmaceutically acceptable salt of the respective SNP having a low degree of solubility in body fluids, for example the tannic or pamoic acid salts described above, or they may contain the SNP in the form of a water-soluble salt thereof together with a protective carrier which prevents rapid release. In the latter case, for example, the SNP may be formulated with a non-antigenic, partially hydrolyzed gelatin in the form of a viscous liquid; or the SNP may be adsorbed on a pharmaceutically acceptable solid carrier, for example zinc hydroxide, and may be administered in suspension in a pharmaceutically acceptable liquid vehicle; or the SNP may be formulated in gels or suspensions with a protective non-antigenic hydrocolloid, e.g. sodium carboxymethylcellulose, polyvinylpyrrolidone, sodium alginate, gelatine, polygalacturonic acids, for example pectin, or certain mucopolysaccharides, together with aqueous or nonaqueous pharmaceutically acceptable liquid vehicles, preservatives, or surfactants. Examples of such formulations are found in standard pharmaceutical texts, e.g., in Remington's Pharmaceutical Sciences cited above. Long-acting, slow-release preparations of the SNP of this invention may also be obtained by microencapsulation in a pharmaceutically acceptable coating material, for example, gelatine, polyvinyl alcohol, or ethyl cellulose. Further examples of coating materials and of the processes used for microencapsulation are described by J. A. Herbig in Encyclopedia of Chemical Technology, Vol. 13, 2nd Ed., Wiley, New York 1967, p. 436 ff. The SNP of this invention may advantageously also be formulated in poly(d,l-lactide) microspheres such as described, e.g., in U.S. Pat. No. 3,773,919 or by Benita et al., 1984 J. Pharm. Sci. 73, 1721, or they may be microencapsulated in lactic-glycolic acid polymers as described in "Lactic-Glycolic Acid Polymers in Drug Carriers in Biology and Medicine", D. L. Wise et al., Eds., Academic Press, Orlando, FLA. 1979. Controlled slow-release preparations of the SNP may also be obtained by formulating them with the new microporous polypropylene polymers as described by Kruisbrink et al., 1984 J. Pharm. Sci. 73, 1713. Alternatively, the SNP of this invention may also be formulated for controlled long-term release in synthetic liposomes such as described, e.g., by Gregoriadis, 1976 New Engl. J. Med. 295, 704 and ibid. 765. All the above preparations for controlled long-term release are designed to release from about 0.01 to about 25 mcg per kilogram body weight per day and are preferably administered by intramuscular injection. Some of the solid dosage forms of the SNP of this invention described above, for example some of the sparingly water-soluble salts thereof, or dispersions in or adsorbates on solid carriers therefor, for example dispersions in a neutral hydrogel of a polymer of ethylene glycol methacrylate or similar monomers cross-linked as described in U.S. Pat. No. 3,551,556, may also be formulated in the form of pellets releasing about the same amounts of SNP as shown above and may be implanted subcutaneously or intramuscularly. Furthermore, sterile aqueous solutions of the SNP of this invention and containing preservatives and other solutes so as to make them isotonic may also be administered intravenously in a continuous manner by means of a minipump attached to the body of the patient, or said minipump may be governed by the action of a sensor attached to or implanted in the body of the patient which activates the minipump whenever the blood pressure of the patient or the concentration of $Na^+$ in his bloodstream exceed a certain predetermined safe limit. Conjugates of the SNP of this invention with albumin are also useful as long-acting dosage forms thereof.

The following Examples will further illustrate this invention.

EXAMPLE 1

The SNP of formula 1 in which $R^1$ is D-Tyr, $R^2$ is Ile, and $R^3$ is OH is prepared by solid-phase synthesis using a 4-(hydroxymethyl)-phenylacetamidomethyl (PAM) resin as suppport and using the Model 430A automatic peptide synthesizer supplied by Applied Biosystems (Foster City, CA), as well as the programs supplied by Applied Biosystems for each individual amino acid. The α-amino groups of all amino acids is protected by the Boc group, the β-carboxyl group of aspartic acid and the β-hydroxy group of serine are protected by the benzyl group, the phenolic hydroxy group of tyrosine is protected by the 2-bromobenzyloxycarbonyl group, the guanidino group of arginine is protected by the tosyl group, the sulfhydryl group of cysteine is protected by the 4-methylbenzyl group. All the protected amino acids are coupled using a two-fold excess of their respective symmetrical anhydrides which are prepared separately from the protected amino acid and DCC, except for Boc-Asn, Boc-Gln, and Boc-Arg(Tos) which are coupled as their respective HOBT esters, also separately prepared from said last-named three protected amino acids by reaction with HOBT and DCC in solution DMF, and double coupling is used for coupling the above HOBT esters to the preceding amino acid or peptide attached to the resin support. Prior to any coupling step the N-terminal protective Boc group of the amino acid or peptide attached to the resin support is cleaved by treatment with 50% TFA in methylene chloride followed by neutralization with N,N'-diisopropylethylamine and replacement of the methylene chloride (DCM) by DMF. The actual coupling step is then carried out in DMF.

Boc-Tyr(2-bromobenzyloxycarbonyl)-(PAM resin), 1.0 g containing 0.5 mmole of the protected amino acid as obtained from Applied Biosystems, is suspended in DMF and the suspension thus obtained is transferred to the reaction vessel. DMF is drained and replaced by DCM, and a solution of TFA (50%) in DCM is added. The mixture is agitated for about 2 minutes, the liquids are drained and replaced by fresh DCM, and the above treatment with 50% TFA in DCM is repeated. The mixture is neutralized by addition of N,N'-diisopropylethylamine (DIEA), agitated for about 15 minutes, the liquids are drained and replaced by fresh DCM, and the above neutralization step is repeated three times. The liquids are drained, the solids are washed three times with DMF, and finally suspended in DMF. During the time taken for the above procedures Boc-Arg(Tos)-OH (0.5 mmole) in DMF is placed in the activator vessel, HOBT and DCC are added and the formation of the HOBT ester is allowed to proceed with agitation over the next 25 minutes. The mixture is then transferred to the reaction vessel where the coupling with H-Tyr(2-bromobenzyloxycarbonyl)-(PAM resin) in DMF prepared as described above is allowed to proceed for about 40 minutes; the above procedures are repeated once, to obtain Boc-Arg(Tos)-Tyr(2-bromobenzyloxycarbonyl)-(PAM resin). The DMF is drained, the solids are washed repeatedly with DCM and then subjected to the same treatment with 50% TFA in DCM as described above, to obtain H-Arg(Tos)-Tyr(2-bromobenzyloxycarbonyl)-(PAM resin). For the coupling of the subsequent phenylalanine residue to said last-named peptide-(PAM resin), Boc-Phe-OH (1.0 mmole) in solution in DCM is treated in the activator vessel with DCC for about 10 minutes and the resulting solution of the symmetrical anhydride Boc-Phe-O-Phe-Boc is transferred to the concentrator vessel where the DCM is evaporated and replaced by DMF. The resulting solution of Boc-Phe-O-Phe-Boc is then transferred to the reaction vessel where the coupling with said last-named peptide-(PAM resin) is allowed to proceed in DMF for about 20 minutes, to obtain Boc-Phe-Arg(Tos)-Tyr(2-bromobenzyloxycarbonyl)-(PAM resin). The DMF is drained, the solids are washed repeatedly with DCM and subjected to the same treatment with 50% TFA in DCM as described above to obtain the tripeptide-(PAM resin), viz., H-Phe-Arg(Tos)-Tyr(2-bromobenzyloxycarbonyl)-(PAM resin). The above procedures are continued, adding successively the appropriate protected amino acids in the desired sequence, whereby all protected amino acids are coupled as their respective symmetrical anhydrides prepared in the manner described above, except for Boc-Asn and Boc-Gln which are coupled as their respective HOBT esters, also prepared in the manner described above. The activator and the concentrator vessels are thoroughly washed with DCM or DMF, as required, before each successive charge with the respective protected amino acid which is to be coupled next in the sequence. All operations are carried out at 25° C. except for the preparation of the HOBT esters of Boc-Arg(Tos), Boc-Asn, and Boc-Gln which are carried out at 10° C., and all operations are performed under nitrogen. Coupling times are increased as the length of the peptide chain increase, by adding 10 seconds times the cycle number of the respective protected amino acid which is being coupled. When all the remaining 20 protected amino acids have been coupled to the above tripeptide-(PAM resin) there is obtained the protected tricosapeptide-(PAM resin) having the sequence of the SNP of formula 1 in which $R^1$ is D-Tyr and $R^2$ is Ile which is thoroughly washed with DCM and dried in vacuo (2.5 g).

The tricosapeptide-(PAM resin) obtained as above is suspended in 2.5 ml anisole in an apparatus suitable for use with HF, preferably in the apparatus supplied by Peptide Institute Inc., Osaka, Japan, and the above suspension is cooled in a dry ice/methanol bath. HF (22.5 ml) is distilled into the apparatus which is then placed in an ice bath for 45 minutes, and then cooled again in a dry ice/methanol bath. The contents are carefully dropped into 300 ml of cold ($-20°$ C.) diethyl ether and the resulting precipitate, a mixture of tricosapeptide and resin, is filtered. The solids are taken up in 50 ml of 80% aqueous acetic acid, filtered, washed with water, and the combined filtrates and washings are diluted with water to 400 ml and freeze-dried. The resulting residue is dissolved in water, the pH is adjusted to pH 6-7, and an aqueous solution of 0.05N potassium ferricyanide is added dropwise with agitation until a yellow colour persists (about 10 ml). The yellow solution is stirred with an anion exchange resin, preferably about 20 ml of IRA-402 (Rohm & Haas) in its acetate form, for about 5 minutes, filtered, and freeze-dried. The residue thus obtained is dissolved in 50% aqueous acetic acid and desalted on a column of Sephadex G-15 (100×2.5 cm) by elution with 50% aqueous acetic acid. The eluates are monitored at 215 nm and the fractions exhibiting absorption are pooled and freeze-dried, to obtain approximately 1 g of the SNP of formula 1 in which $R^1$ is H-D-Tyr, $R^2$ is Ile, and $R^3$ is OH, in the crude state.

Further purification of the crude SNP obtained as described above is carried out by RP-HPLC on a Waters Prep 500 apparatus (Waters Associates, Melford, MA) using a Vydac C-18, 15-20 micron, 300 A preparative cartridge, by gradient elution with solvent A (0.25N $H_3PO_4$ titrated to pH 2.25 with triethylamine) and solvent B (solvent A/acetonitrile 40/60. The effluents are monitored at 215 nm and fractions with a high degree of absorption are collected. Samples thereof are checked for their respective degree of purity by RP-HPLC on an analytical apparatus (Varian LC5500, Varian Instruments, Palo Alto, CA) using a Vydac C-18, 5 micron, 300 A column, and the results obtained are also used to establish the optimal conditions of flow rate and of the slope and the end points of the gradient for the above preparative apparatus. Final purification is carried out by RP-HPLC on a Varian LC5500 apparatus using a Vydac C-18, 5 micron, 300 A column (250×4.6 mm), with monitoring at 215 nm. At a flow rate of 1.5 ml/min and using the same solvent system as above with a gradient of solvent B from 30% to 50% over a period of 40 minutes there is obtained at 4.156 minutes after the start of the gradient a minor impurity accounting for 0.144% of the total substance. The major part of the SNP appears at 20.494 minutes after the start of the gradient as a single symmetrical peak accounting for 99.856% of the total substance. In terms of the gradient used the above peak appears at 39.5% of solvent B. Applying the above conditions to the preparative apparatus, the fractions eluted between 38% and 41% of solvent B are pooled, evaporated, taken up in 5% aqueous acetic acid and desalted on the same type of cartridge as used above (Vydac C-18, 15-20 micron, 300A) by elution with 5% aqueous acetic acid containing 5% acetonitrile. The eluates thus obtained are diluted with water and freeze-dried, to obtain the SNP of formula 1 in which $R^1$ is H-D-Tyr, $R^2$ is Ile, and $R^3$ is OH as the acetate salt thereof, with a degree of purity of better than 99.8%. The yields obtained in a number of runs are consistently between 30 mg and 40 mg.

Amino acid analysis confirms the above composition: Asp 2.03 (2), Ser 1.76 (2), Gln 1.05 (1), Gly 5.27 (5), Ala 1.04 (1), Cys 1.85 (2), Ile 1.92 (2), Leu 0.99 (1), Tyr 1.93 (2), Phe 2.00 (2), Arg 3.15 (3).

When proceeding in the same manner as described above, optionally replacing $R^1$ as H-D-Tyr by $R^1$ as H-D-Trp, H-D-phenylglycyl, or H-D-t-butylglycyl, respectively, and/or replacing $R^2$ as Ile by $R^2$ by Met, the following SNP of formula 1 in which $R^3$ is OH are respectively obtained:

| $R^1$ | $R^2$ | $R^3$ |
|---|---|---|
| H—D-Trp | Ile | OH |
| H—D-phenylglycyl | Ile | OH |
| H—D-t-butylglycyl | Ile | OH |
| H—D-Tyr | Met | OH |
| H—D-Trp | Met | OH |
| H—D-phenylglycyl | Met | OH |
| H—D-t-butylglycyl | Met | OH |

Also when proceeding in the same manner as described above, but replacing the 4-(hydroxymethyl)-phenylacetamidomethyl (PAM) resin by a 4-methylbenzhydrylamine resin as the resin support there is obtained the SNP of formula 1 in which $R^1$ is H-D-Tyr, $R^2$ is Ile, and $R^3$ is $NH_2$ as the acetate salt thereof.

Furthrmore, when proceeding as described above replacing the 4-(hydroxymethyl)-penylacetamidomethyl (PAM) resin by a 4-methylbenzhydrylamine resin as the resin support and optionally replacing $R^1$ as H-D-Tyr by $R^1$ as H-D-Trp, H-D-phenylglycyl, or H-D-t-butylglycyl, respectively, and/or replacing $R^2$ as Ile by $R^2$ as Met, the following SNP of formula 1 in which $R^3$ is $NH_2$ are respectively obtained:

| $R^1$ | $R^2$ | $R^3$ |
|---|---|---|
| H—D-Trp | Ile | $NH_2$ |
| H—D-phenylglycyl | Ile | $NH_2$ |
| H—D-t-butylglycyl | Ile | $NH_2$ |
| H—D-Tyr | Met | $NH_2$ |
| H—D-Trp | Met | $NH_2$ |
| H—D-phenylglycyl | Met | $NH_2$ |
| H—D-t-butylglycyl | Met | $NH_2$ |

EXAMPLE 2

Effects upon Urine Flow and Electrolyte Excretion

The SNP of formula 1 in which $R^1$ is H-D-Tyr, $R^2$ is Ile, and $R^3$ is OH is tested under the code number 05-22-0318 and its effects are compared with those exhibited by a known ANP composed of 28 amino acid residues and identified by the code number BG-3009. Details of the assay method are described above, and it remains only to be stated that 8 male normotensive Sprague-Dawley rats are used in each group. Results are shown in Tables 1 and 2, and it is seen that the above SNP causes an immediate pronounced diuresis which reaches its maximum during the first ten minutes. Urine flow then decreases sharply and is at control volumes at about 40 minutes where it remains until about 140 minutes. However, from 150 minutes to the end of the experiment the above SNP causes a marked rise in urine flow when compared to control values. Although the reference compound BG-3009 shows similar effects up to 130 minutes, the increase in urine volume observed thereafter is hardly noticeable and may not be significant. Both compounds are tested at dosages of 3.5 mcg/kg and both cause short-lasting decreases in $K^+$ and $Cl^-$ excretion returning to control values after about 60 minutes. Both compounds cause sharp increases in $Na^+$ excretion for the first 30–40 minutes, returning to control values thereafter, and followed by a slight increase in $Na^+$ and $Cl^-$ excretion from about 140–160 minutes to the end of the experiment at 240 minutes which is more marked with the above SNP than with the reference compound BG-3009, which is identical with the ANP described by Flynn et al., cited above.

TABLE 1

| CODE No. | CONTROLS | | | URINE FLOW (ml./min./kg. body wt × $10^{-3}$) | | | | | | | (MINUTES) |
| --- | --- | --- | --- | --- | --- | --- | --- | --- | --- | --- | --- |
| | 10 | 20 | 30 | 10 | 20 | 30 | 40 | 50 | 60 | 70 | 80 |
| 05-22-0318 | 16.1 ± 2.7 | 14.6 ± 1.7 | 12.2 ± 2.0 | 357.4 ± 34.8 | 46.4 ± 9.1 | 22.0 ± 2.5 | 17.9 ± 2.1 | 18.2 ± 1.9 | 16.6 ± 1.4 | 18.2 ± 1.7 | 18.1 ± 1.0 |
| BG3009 | 22.0 ± 5.3 | 19.9 ± 6.8 | 13.6 ± 2.3 | 333.7 ± 42.7 | 55.7 ± 6.7 | 23.3 ± 3.9 | 16.4 ± 4.2 | 16.9 ± 3.3 | 16.7 ± 2.9 | 16.4 ± 2.4 | 16.4 ± 2.4 |

| CODE No. | CONTROLS | | | URINE FLOW (ml./min./kg. body wt × $10^{-3}$) | | | | | | | (MINUTES) |
| --- | --- | --- | --- | --- | --- | --- | --- | --- | --- | --- | --- |
| | 10 | 20 | 30 | 90 | 100 | 110 | 120 | 130 | 140 | 150 | 160 |
| 05-22-0318 | 16.1 ± 2.7 | 14.6 ± 1.7 | 12.2 ± 2.0 | 13.3 ± 1.5 | 18.1 ± 1.2 | 17.9 ± 1.4 | 19.2 ± 2.9 | 17.4 ± 2.6 | 18.3 ± 1.9 | 25.4 ± 3.7 | 22.6 ± 2.3 |
| BG3009 | 22.0 ± 5.3 | 19.9 ± 6.8 | 13.6 ± 2.3 | 15.2 ± 2.2 | 16.0 ± 1.6 | 17.2 ± 2.4 | 17.6 ± 1.9 | 23.4 ± 4.1 | 22.6 ± 2.0 | 21.4 ± 1.9 | 19.7 ± 1.7 |

| CODE No. | CONTROLS | | | URINE FLOW (ml./min./kg. body wt × $10^{-3}$) | | | | | | | (MINUTES) |
| --- | --- | --- | --- | --- | --- | --- | --- | --- | --- | --- | --- |
| | 10 | 20 | 30 | 170 | 180 | 190 | 200 | 210 | 220 | 230 | 240 |
| 05-22-0318 | 16.1 ± 2.7 | 14.6 ± 1.7 | 12.2 ± 2.0 | 25.2 ± 3.0 | 30.4 ± 4.4 | 26.7 ± 3.3 | 26.5 ± 3.4 | 25.0 ± 4.1 | 19.1 ± 2.2 | 23.4 ± 2.7 | 20.5 ± 3.8 |
| BG3009 | 22.0 ± 5.3 | 19.9 ± 6.8 | 13.6 ± 2.3 | 19.9 ± 1.2 | 20.5 ± 1.9 | 22.3 ± 2.6 | 22.3 ± 1.7 | 20.7 ± 2.6 | 22.7 ± 2.4 | 28.6 ± 8.0 | 25.9 ± 5.6 |

TABLE 2

| | CONTROLS | | | ELECTROLYTE EXCRETION (mmol/l./gm. kidney tissue) $8^d$ rats | | | | | | | COMPOUND #05-22-0318 (MINUTES) | | | | |
| --- | --- | --- | --- | --- | --- | --- | --- | --- | --- | --- | --- | --- | --- | --- | --- |
| | 10 | 20 | 30 | 10 | 20 | 30 | 40 | 50 | 60 | 70 | 80 | 90 | 100 | 110 | 120 |
| $Na^+$ | 5.7 | 4.6 | 3.5 | 7.7 | 11.1 | 7.8 | 5.9 | 4.3 | 3.4 | 3.1 | 2.6 | 2.0 | 2.1 | 2.2 | 2.7 |
| $K^+$ | 7.1 | 7.2 | 7.5 | 1.5 | 3.0 | 4.5 | 6.3 | 6.6 | 6.7 | 7.1 | 7.5 | 7.9 | 7.6 | 7.6 | 7.4 |
| $Cl^-$ | 13.5 | 14.9 | 15.3 | 8.1 | 12.6 | 11.0 | 12.6 | 12.2 | 11.9 | 12.9 | 12.7 | 12.1 | 12.0 | 11.9 | 11.9 |
| | | | | | | | | | BG3009 | | | | | | |
| $Na^+$ | 6.8 | 6.7 | 6.4 | 10.0 | 13.2 | 12.4 | 11.1 | 8.8 | 7.8 | 7.1 | 6.5 | 6.4 | 6.3 | 6.5 | 6.7 |
| $K^+$ | 7.8 | 8.3 | 8.3 | 1.5 | 2.4 | 4.9 | 5.6 | 6.6 | 7.4 | 7.7 | 7.9 | 8.0 | 8.2 | 8.2 | 8.5 |
| $Cl^-$ | 12.1 | 13.5 | 14.9 | 10.1 | 12.8 | 12.7 | 13.0 | 14.0 | 13.5 | 13.7 | 13.0 | 13.3 | 13.3 | 13.1 | 13.7 |

| | CONTROLS | | | ELECTROLYTE EXCRETION (mmol/l./gm. kidney tissue) $8^d$ rats | | | | | | | COMPOUND #05-22-0318 (MINUTES) | | | | |
| --- | --- | --- | --- | --- | --- | --- | --- | --- | --- | --- | --- | --- | --- | --- | --- |
| | 10 | 20 | 30 | 130 | 140 | 150 | 160 | 170 | 180 | 190 | 200 | 210 | 220 | 230 | 240 |
| $Na^+$ | 5.7 | 4.6 | 3.5 | 2.8 | 3.3 | 4.3 | 5.5 | 7.2 | 6.9 | 7.0 | 7.1 | 6.5 | 6.0 | 5.9 | 6.1 |
| $K^+$ | 7.1 | 7.2 | 7.5 | 7.5 | 7.7 | 7.8 | 8.0 | 7.4 | 7.2 | 7.3 | 7.2 | 7.3 | 7.3 | 7.2 | 6.8 |
| $Cl^-$ | 13.5 | 14.9 | 15.3 | 11.9 | 12.6 | 14.0 | 15.2 | 14.0 | 13.3 | 15.8 | 16.6 | 16.7 | 18.0 | 18.0 | 17.5 |
| | | | | | | | | | BG3009 | | | | | | |
| $Na^+$ | 6.8 | 6.7 | 6.4 | 6.6 | 7.0 | 7.3 | 7.4 | 7.7 | 8.3 | 8.7 | 9.2 | 9.6 | 9.4 | 9.2 | 9.2 |
| $K^+$ | 7.8 | 8.3 | 8.3 | 8.6 | 9.0 | 9.4 | 9.4 | 9.2 | 9.1 | 8.7 | 8.5 | 8.4 | 8.3 | 8.3 | 8.5 |
| $Cl^-$ | 12.1 | 13.5 | 14.9 | 13.6 | 14.8 | 15.2 | 14.2 | 14.4 | 14.8 | 14.4 | 14.7 | 15.0 | 15.3 | 14.8 | 15.7 |

EXAMPLE 3

Vasorelaxant Activities

The SNP of formula 1 in which $R^1$ is H-D-Tyr, $R^2$ is Ile, and $R^3$ is OH, identified by the code number 05-22-0318 is tested for its vasorelaxant activities and compared with a known ANP composed of 28 amino acid residues and identified by the code number BG-3009. The test method is described above in some detail. Two rabbits are sacrificed and the thoracic aorta prepared from each animal is helically cut so as to obtain five strips from each aorta. One strip from each aorta is used for time control and is exposed to the full range of concentrations of noradrenaline alone at the beginning and at the end of the experiment, and the concentrations of noradrenaline giving 50% of the maximal response are calculated (EC50). One of the above two time control strips gives an EC50 of 1.5, the other gives an EC50 of 2.2, thus proving that there is no significant loss of response during the time of the experiment, and that there are no significant differences in the responses to noradrenaline alone given by the strips from two different animals. One strip from each of the remaining two pairs of strips from each aorta is then exposed to the full range of concentrations of noradrenaline alone as described above, and the responses are noted. The other strip from the same pair is first exposed to concentrations of 2, 5, 50, and 500 ng/ml of the compound to be tested, respectively, and five minutes after having added the above concentrations of the compound to be tested the strip is challenged with noradrenaline at increasing concentrations and the responses obtained are noted again. The EC50 obtained in the presence of the respective concentration of the compound to be tested is then divided by the EC50 obtained in the absence of said compound with noradrenaline alone, and the ratio of the two EC50's is calculated to give a clear measure of the vasorelaxant properties of said compound. Furthermore, when taking the potency of the reference compound having the code number BG-3009 arbitrarily as 100 the relative potencies of the above SNP (code No. 05-22-0318) at the respective levels of concentration are also calculated. Results are shown in Table 3 and indicate that the vasorelaxant effects of the above SNP are not significantly different from those obtained with the reference compound.

TABLE 3

| Compound | Concentration, ng/ml | Ratio | Relative Potency |
|---|---|---|---|
| None(+) | — | 1.5, 2.2 | — |
| 5-22-0318 | 2 | 2.2 | 76 |
| 5-22-0318 | 5 | 2.4 | 63 |
| 5-22-0318 | 50 | 13.5 | 52 |
| 5-22-0318 | 500 | 14.4 | 55 |
| BG-3009 | 2 | 2.9 | 100 |
| BG-3009 | 5 | 3.8 | 100 |
| BG-3009 | 50 | 25.8 | 100 |
| BG-3009 | 500 | 26.1 | 100 |

(+)Time Control

We claim:

1. A peptide of the formula:

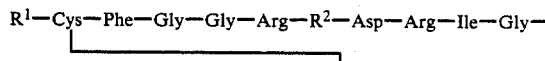
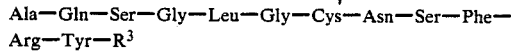

Ala—Gln—Ser—Gly—Leu—Gly—Cys—Asn—Ser—Phe—Arg—Tyr—R³ in which
R¹ is a D-amino acid selected from the group consisting of Ala, Asn, Asp, Cys, Gln, Glu, His, Ile, Trp, Tyr, PheGly & t-BuGly
R² is selected from Ile and Met and R³ is selected from OH and NH₂ and the pharmacologically acceptable acid addition salt thereof.

2. A peptide of claim 1 in which R¹ is selected from D-Tyr, D-Trp, D-PheGly and D-t-BuGly.

3. A peptide of claim 2 in which R³ is OH.

4. A peptide of claim 2 in which R³ is NH₂.

5. A peptide of claim 2 in which R¹ is H-D-Tyr, R² is Ile, and R³ is OH.

6. A peptide of claim 2 in which R¹ is H-D-Tyr, R² is Ile, and R³ is NH₂.

7. The acetate salt of the peptide of claim 5 in which R¹ is H-D-Tyr, R² is Ile, and R³ is OH.

* * * * *